(12) United States Patent
Sakaguchi et al.

(10) Patent No.: US 9,713,555 B2
(45) Date of Patent: Jul. 25, 2017

(54) DISPOSABLE DIAPER WITH MEANDERING LEG HOLE STRETCH UNITS

(71) Applicant: UNICHARM CORPORATION, Shikokuchuo-shi, Ehime (JP)

(72) Inventors: Satoru Sakaguchi, Kanonji (JP); Kana Sawa, Kanonji (JP); Yasuhiro Yamanaka, Kanonji (JP)

(73) Assignee: UNICHARM CORPORATION, Ehime (JP)

( * ) Notice: Subject to any disclaimer, the term of this patent is extended or adjusted under 35 U.S.C. 154(b) by 104 days.

(21) Appl. No.: 14/380,194

(22) PCT Filed: Mar. 28, 2013

(86) PCT No.: PCT/JP2013/059339
§ 371 (c)(1),
(2) Date: Aug. 21, 2014

(87) PCT Pub. No.: WO2013/147060
PCT Pub. Date: Oct. 3, 2013

(65) Prior Publication Data
US 2015/0025490 A1 Jan. 22, 2015

(30) Foreign Application Priority Data
Mar. 30, 2012 (JP) .................. 2012-083040

(51) Int. Cl.
*A61F 13/49* (2006.01)
*A61F 13/494* (2006.01)

(52) U.S. Cl.
CPC .. *A61F 13/49017* (2013.01); *A61F 13/49406* (2013.01); *A61F 2013/49088* (2013.01); *A61F 2013/49092* (2013.01)

(58) Field of Classification Search
CPC .............. A61F 13/49017; A61F 13/494; A61F 13/49406; A61F 13/49413; A61F 13/4942;
(Continued)

(56) References Cited

U.S. PATENT DOCUMENTS 4,906,243 A * 3/1990 Dravland .......... A61F 13/49009
604/385.21
5,167,897 A * 12/1992 Weber ............... A61F 13/15593
264/101

(Continued)

FOREIGN PATENT DOCUMENTS

JP  10-243961 A  9/1998
JP  11-047189 A  2/1999
(Continued)

OTHER PUBLICATIONS

Office Action dated Jun. 24, 2015, corresponding to Chinese patent application No. 201380016277.7.
(Continued)

*Primary Examiner* — Kathryn E Ditmer
(74) *Attorney, Agent, or Firm* — Hauptman Ham, LLP (57) ABSTRACT

A disposable diaper 10 has sheet-like leg hole stretch units 100 that extend in a product lengthwise direction L in an area where leg hole concave units 35 are formed and are at least partially stretchable along a product lengthwise direction L. End edges in a product widthwise direction W of the leg hole stretch units 100 meander in the product lengthwise direction L. Distances between the end edges in the product widthwise direction W of the leg hole stretch units 100 and a center line CL change from a front waistline unit 20 toward a rear waistline unit 30. Provided are a plurality of inflection points where an amount of change in the distance starts decreasing instead of increasing and a plurality of inflection (Continued)

points where an amount of change in the distance starts increasing instead of decreasing, respectively.

14 Claims, 5 Drawing Sheets

(58) Field of Classification Search
CPC .. A61F 2013/49068; A61F 2013/49074; A61F 2013/49079; A61F 2013/49082; A61F 2013/49433; A61F 2013/4948
See application file for complete search history.

(56) References Cited

U.S. PATENT DOCUMENTS

| | | | | |
|---|---|---|---|---|
| 5,527,302 | A * | 6/1996 | Endres | A61F 13/49009 604/382 |
| 5,662,637 | A * | 9/1997 | Kitaoka | A61F 13/4942 604/385.28 |
| 6,022,338 | A * | 2/2000 | Putzer | A61F 13/4942 604/378 |
| 6,607,515 | B2 * | 8/2003 | Glaug | A61F 13/49 604/385.01 |
| 6,890,630 | B2 * | 5/2005 | Franklin | A61F 13/15593 428/138 |
| 6,939,334 | B2 * | 9/2005 | Odorzynski | A61F 13/4902 156/244.25 |
| 7,959,618 | B2 * | 6/2011 | Hermansson | A61F 13/496 604/385.01 |
| 8,382,735 | B2 | 2/2013 | Torigoshi et al. | |
| 2005/0065491 | A1 * | 3/2005 | Schneider | A61F 13/15203 604/385.01 |
| 2006/0150302 | A1 * | 7/2006 | Warren | A41B 9/001 2/400 |
| 2009/0030392 | A1 * | 1/2009 | Kanai | A61F 13/15203 604/385.01 |
| 2010/0228212 | A1 * | 9/2010 | Desai | A61F 13/15203 604/367 |
| 2011/0118690 | A1 * | 5/2011 | Oku | A61F 13/49011 604/385.16 |
| 2013/0197463 | A1 * | 8/2013 | Malowaniec | A61F 13/49014 604/386 |

FOREIGN PATENT DOCUMENTS

| | | |
|---|---|---|
| JP | 2006-42941 A | 2/2006 |
| JP | 2006-166941 A | 6/2006 |

OTHER PUBLICATIONS

Japanese Office Action in corresponding Japanese Patent Application No. 2012-083040 dated Feb. 26, 2013.
International Search Report mailed Jun. 18, 2013 in International Patent Application No. PCT/JP2013/059339, filed Mar. 28, 2013.
Office Action in EA Patent Application No. 201400872, dated Apr. 15, 2016.
Office Action in AU Patent Application No.: 2013241113, dated Mar. 16, 2017.

* cited by examiner

DISPOSABLE DIAPER WITH MEANDERING LEG HOLE STRETCH UNITS

RELATED APPLICATIONS

The present application is a National Phase of International Application Number PCT/JP2013/059339, filed Mar. 28, 2013, which claims priority to Japanese Application Number 2012-083040, filed Mar. 30, 2012.

TECHNICAL FIELD

The present invention relates to a disposable diaper having side flaps at end sides in a product widthwise direction of an absorbent body, and, in particular, to a disposable diaper with which it is possible to ensure that the irritation to a skin around leg holes of a wearer, caused due to elastic members at side flaps, is weakened.

BACKGROUND ART

Conventionally, various attempts have been made on disposable diapers to provide excellent wearing comfort while completely preventing leakage of bodily waste. For example, a disposable diaper is known that is configured to have a distance between a pair of leg hole elastic members at a front waistline unit greater than a distance between the elastic members at a rear waistline unit (see Patent Literature 1).

According to such a disposable diaper, a pocket (extra room) is formed at the front waistline unit, so that an absorber large enough to completely absorb bodily waste can be arranged at the front waistline unit. Consequently, it is considered that the diaper can effectively prevent leakage from the front waistline unit where urine excretion is substantially large.

CITATION LIST

Patent Literature

[PTL 1]
Japanese Unexamined Patent Application Publication No. H11-47189 (FIG. 1)

SUMMARY OF INVENTION

Technical Problem

However, the aforementioned conventional disposable diaper had the below problems. Specifically, since the leg hole elastic member is arranged at the side edges in the widthwise direction of the product, there is a problem in that the member is likely to dig into a wearer's skin and thus irritate the skin. In particular, in case of a disposable diaper for babies, their skin is so thin (with a thin keratose layer) that their level of tolerance to the irritation is not high, and a problem easily arises therefrom.

Thus, the present invention is made in consideration of these circumstances, and the object thereof is to provide a disposable diaper that is less irritating to the skin of a wearer around leg holes while prohibiting the leakage of bodily waste completely.

Solution to Problem

A feature of the present invention is summarized as a disposable diaper (disposable diaper 10) has a front waistline unit (front waistline unit 20), a rear waistline unit (rear waistline unit 30), a crotch unit (crotch unit 25), a vertically long absorbent body (absorbent body 15) containing a liquid retaining absorber (absorber 40) and side flaps (side flaps 70) arranged at end sides in the product widthwise direction of the absorbent body, wherein leg hole concave units (leg hole concave units 35) that are recessed toward the center in the product widthwise direction of the absorbent body, are formed at the side flaps. The disposable diaper includes sheet-like leg hole stretch units (leg hole stretch units 100) that are arranged at side edges in the product widthwise direction (product widthwise direction W) of the side flaps, that extend in the product lengthwise direction (product lengthwise direction L) in an area where the leg hole concave units are formed, and that are partially stretchable at least along the product lengthwise direction. End edges in the product widthwise direction of the leg hole stretch units meander in the product lengthwise direction. A distance (for instance, distance d1) between the end edges in the product widthwise direction of the leg hole stretch units and a straight line (central line CL) that passes through the center in the product widthwise direction of the disposable diaper and is parallel to the product lengthwise direction, changes from the front waistline unit toward the rear waistline unit. A plurality of inflection points (for instance, inflection point P2) where an amount of change in the distance starts decreasing instead of increasing, and a plurality of inflection points (for instance, inflection point P1) where an amount of change in the distance starts increasing instead of decreasing, are provided respectively.

Advantageous Effects of Invention

According to the feature of the present invention, provided is a disposable diaper that is less irritating to the skin on a wearer around leg holes while completely prohibiting leakage of bodily waste.

DESCRIPTION OF EMBODIMENTS

Hereinafter, an embodiment of a disposable diaper according to the present invention is described with reference to accompanying drawings. In the following description of the drawings, the same or similar reference numerals are used to designate the same or similar portions. It will be appreciated that the drawings are schematically shown and the ratio and the like of each dimension are different from the real ones.

Accordingly, specific dimensions should be determined in consideration of the explanation below. Moreover, among the drawings, the respective dimensional relations or ratios may differ.

(1) Overall Schematic Configuration of Disposable Diaper

Figure 1:
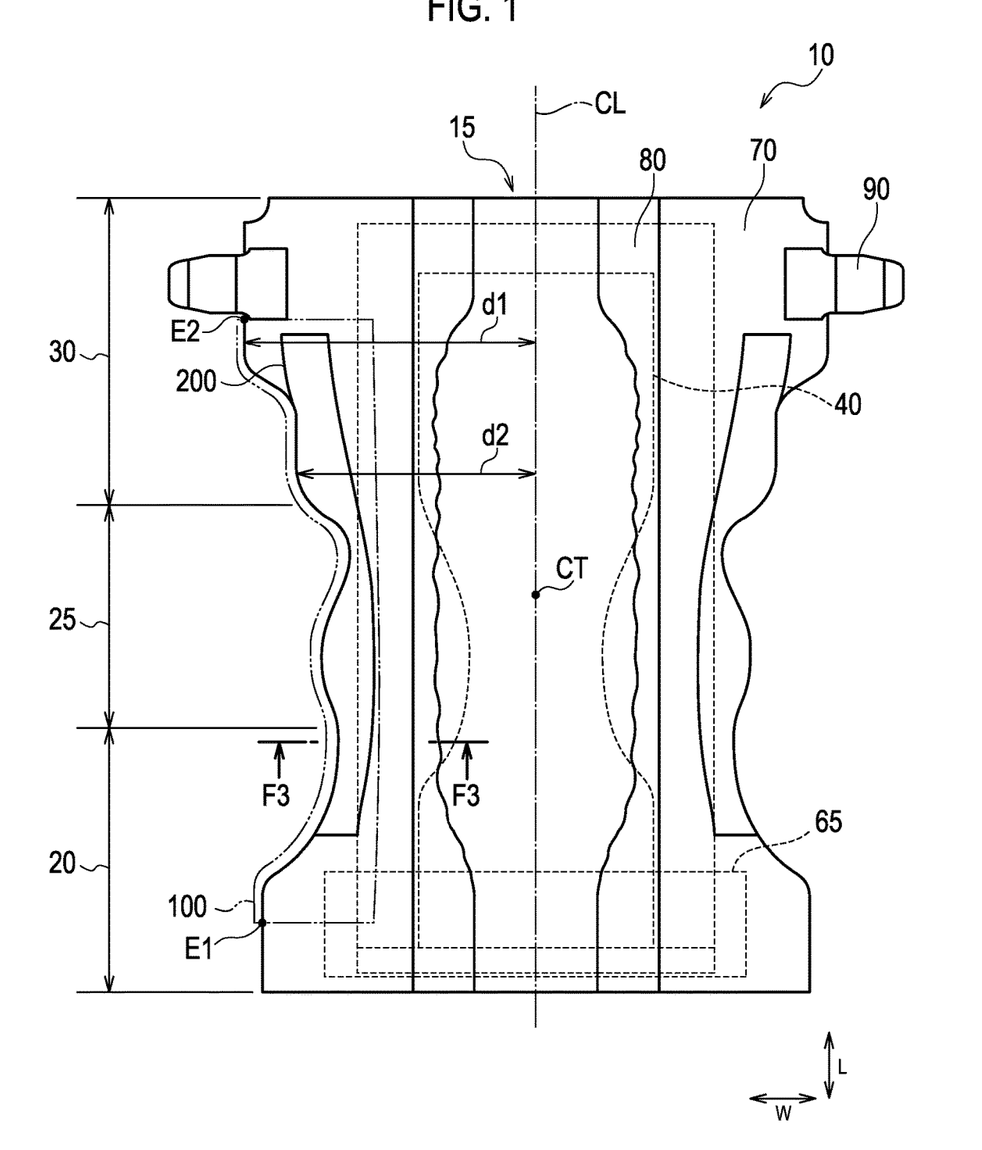
FIG. 1 is a development plan view of a disposable diaper 10 according to an embodiment of the present invention.
Figure 2:
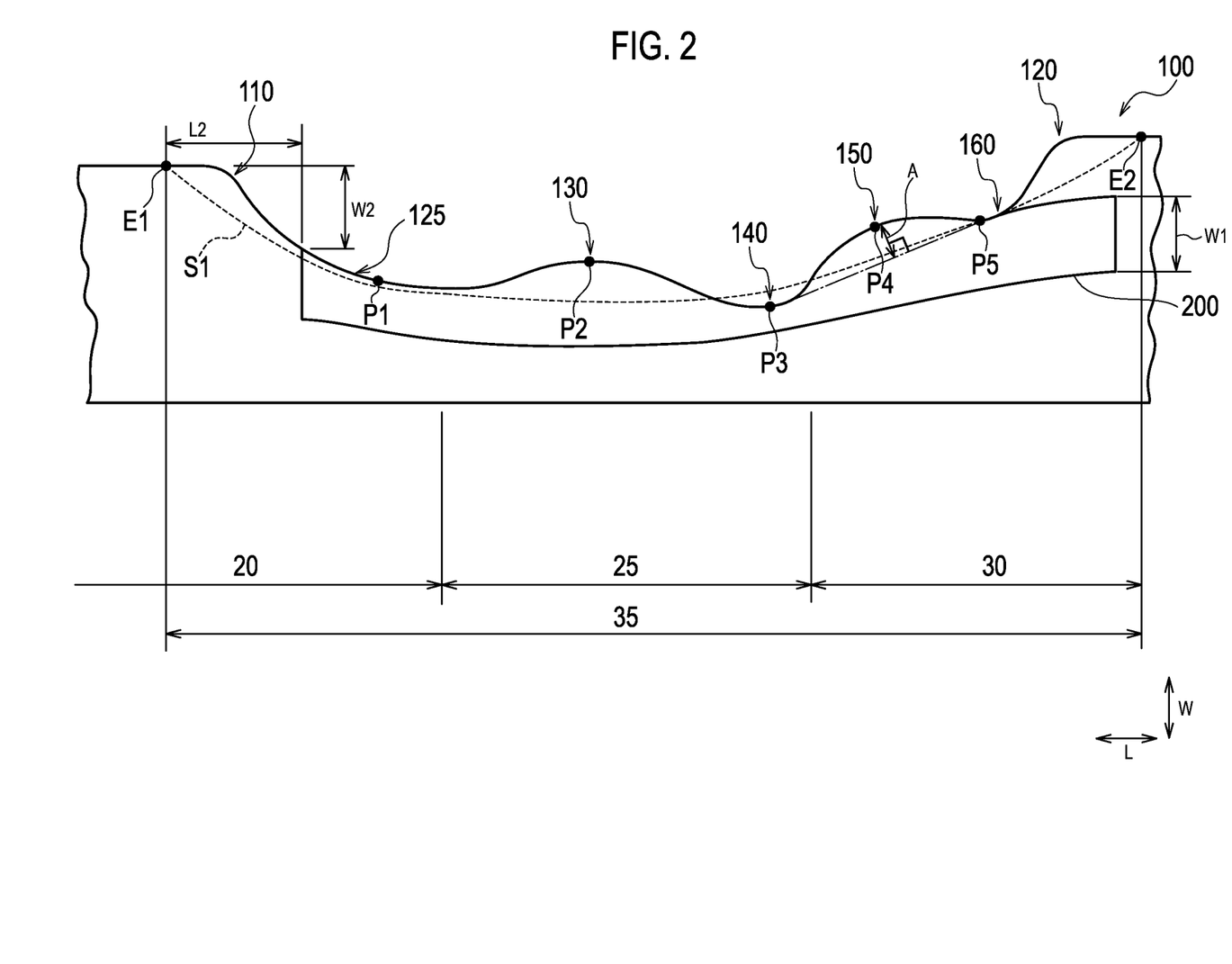
FIG. 2 is an enlarged plan view of a leg hole stretch unit 100 according to the embodiment of the present invention.
Figure 3:
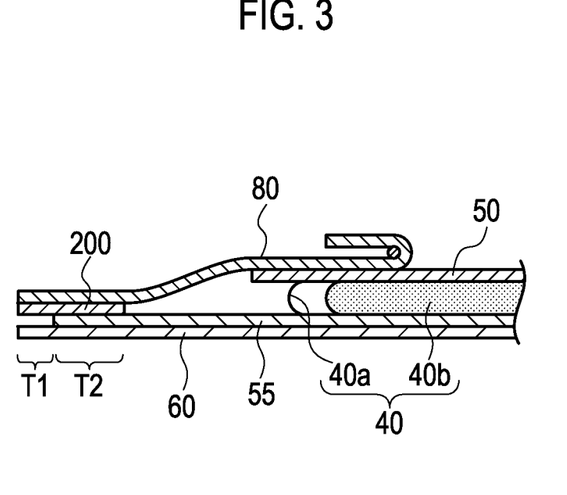
FIG. 3 is a diagram schematically illustrating a cross section of the disposable diaper 10 along the line F3-F3 shown in FIG. 1.

FIG. 1 is a development plan view of a disposable diaper 10 according to the present embodiment. FIG. 2 is an enlarged plan view of a leg hole stretch unit 100. FIG. 3 is a diagram schematically illustrating a cross section of the disposable diaper 10 along the line F3-F3 shown in FIG. 1.

As shown in FIGS. 1 to 3, the disposable diaper 10 has a front waistline unit 20, a crotch unit 25, and a rear waistline unit 30. The front waistline unit 20 is a section that is in contact with the front waistline of a wearer. Additionally, the rear waistline unit 30 is a section that is in contact with the rear waistline of a wearer. The crotch unit 25 is positioned between the front waistline unit 20 and the rear waistline unit 30. An absorbent body 15 is configured by the front waistline unit 20, the crotch unit 25 and the rear waistline unit 30. Additionally, a pair of leg hole concave units 35 are formed at the disposable diaper 10 (see FIG. 4). Specifically, the leg hole concave units 35 are formed at end sides in a product widthwise direction W of the absorbent body 15 (in particular, at side flaps 70), and are recessed toward the center in the product widthwise direction W. The leg hole concave units 35 form openings from the front waistline unit 20 toward the rear waistline unit 30 by engaging fastening tapes 90 at the rear waistline unit 30 with the front waistline unit 20, specifically, target tapes 65 when the disposable diaper 10 is being worn by a wearer.

Moreover, in the present embodiment, a direction from the front waistline unit 20 toward the rear waistline unit 30 is referred to as a product lengthwise direction L, and a direction that is orthogonal to the product lengthwise direction L is described as the product widthwise direction W.

The disposable diaper 10 has an absorber 40 that crosses over the crotch unit 25 and extends to the front waistline unit 20 and the rear waistline unit 30. The absorbent body 15 has a vertically long shape, and includes the liquid retaining absorber 40. The absorber 40 is configured by an absorbent core 40a and a core wrap 40b.

The absorber 40 is the same as that of a conventional disposable diaper, and is appropriately configured of conventional members and materials such as ground pulp and highly absorbent polymer. The absorbent core 40a is wrapped by the sheet-like core wrap 40b. The core wrap 40b is a sheet for wrapping the absorbent core 40a. A part of at least the skin surface side of the core wrap 40b is configured by various nonwoven cloth or a tissue sheet having permeability. For example, an air-through nonwoven cloth, a spunbond nonwoven cloth, or an SMS (spunbond-meltblown-spunbond) nonwoven cloth having a mass of approximately 10 to 30 g/m², or a tissue sheet having a mass of approximately 10 to 30 g/m² can be used.

On the top side (skin contact surface side) of the absorber 40 is provided a liquid-permeable topsheet 50. Also, on the back side (non-skin contact surface side) of the absorber 40, a liquid-impermeable leakage-preventing film 55 is provided. On the back side of the leakage-preventing film 55, a backsheet 60 formed of a nonwoven fabric is provided.

At end sides in the product widthwise direction W of the absorbent body 15, the side flaps 70 are provided from the front waistline unit 20 toward the rear waistline unit 30 respectively. The side flaps 70 are configured of one or two or more pieces of nonwoven fabrics overlapping one another. Furthermore, the fastening tape 90 is provided in each of the pair of side flaps 70.

At side edges in the product widthwise direction W of the side flaps 70, a pair of right and left leg hole stretch units 100 are provided. The leg hole stretch units 100 extend in the product lengthwise direction L in an area where the leg hole concave unit 35 is formed, and are partially stretchable at least along the product lengthwise direction L. In the present embodiment, the leg hole stretch units 100 are an area having a stretch sheet 200 (see FIG. 1), and end edges in the product widthwise direction of the leg hole stretch units 100 meander in the product lengthwise direction L. The stretch sheet 200 is formed of an elastic nonwoven cloth sheet.

Additionally, inside the pair of leg hole stretch units 100 (closer to the center in the product widthwise direction W), a pair of leg side gathers 80 extending in the product lengthwise direction L are provided. Moreover, the disposable diaper 10 may have waist gathers that are arranged along the product widthwise direction W at the front waistline unit 20 and the rear waistline unit 30.

(2) Shape of Leg Hole Stretch Units 100

Subsequently, the shape of the leg hole stretch units 100 and so forth will be explained in detail. As illustrated in FIG. 2, the leg hole stretch units 100 are provided along the end edges of the leg hole concave units 35 of the disposable diaper 10. As mentioned above, the end edges in the product widthwise direction of the leg hole stretch units 100 meander in the product lengthwise direction L. Specifically, as inflection points P1 to P5 are formed at the leg hole stretch units 100, the end edges in the product widthwise direction W of the leg hole stretch units 100 meander. Thus, the end edges in the product widthwise direction of the leg hole stretch units 100 have concavities and convexities in the product widthwise direction W with respect to a curve 51 along the leg holes of a wearer of the disposable diaper 10.

More specifically, distances (distances d1, d2) between the end edges in the product widthwise direction W of the leg hole stretch units 100 and a center line CL (see FIG. 1) that passes through a center in the product widthwise direction W and is parallel to the product lengthwise direction, change from the front waistline unit 20 toward the rear waistline unit 30. Provided are a plurality of inflection points (inflection points P2, P4) where an amount of change in the distances starts decreasing instead of increasing and a plurality of inflection points (inflection points P1, P3, P5) where an amount of change in the distances starts increasing instead of decreasing, respectively.

Here, the distances are measured, when the disposable diaper 10 is in an open expanded condition.

Additionally, the leg hole stretch units 100 can be produced by, for instance, the following method. Specifically, the stretch sheet 200 is extended while being curved along the shape of leg holes, extending over the cutting lines for the front end and back end of the leg hole concave units 35. In this case, the stretch sheet 200 is sandwiched between a sheet configuring the side flaps 70 or the leg side gathers 80 and an outer layer sheet, and is fixed to the sheets with an adhesive. Subsequently, the leg hole stretch units 100 are formed by cutting the stretch sheet 200 and the sheets along the leg hole concave units 35 with a cutter having a predetermined shape.

In the present embodiment, it is preferable that a width W1 along the product widthwise direction W in the natural state of the leg hole stretch units 100 be between 5 mm and 45 mm, more preferably, between 12.5 mm and 40 mm. When below 5 mm, stress from the stretch sheet 200 concentrates and further strains a wearer's skin. On the other hand, at the width above 45 mm, an area along the leg holes becomes too broad in comparison with the total width of the disposable diaper 10, so that the leg hole stretch units 100 can be easily rolled or turned inside toward the body of a wearer.

In addition, the natural state indicates the state when the disposable diaper 10 is taken out from a package and is left for 60 minutes under the atmosphere of 20° C.±2° C. and 60%±5% RH in relative humidity after which it is measured. Also, the degree of stretch of the leg hole stretch units 100 is set between 1.5 times and 2.4 times. By setting the degree of stretch within this range, the leg hole stretch units 100 can properly fit the body of a wearer.

Additionally, the degree of stretch indicates the degree of expansion and contraction in the product widthwise direction W of the leg hole stretch units 100, and is defined as below.

The degree of stretch=(maximum expansion length of the product leg hole stretch units 100)/(length of the product leg hole stretch units 100 in the natural state)

Moreover, the maximum expansion length is the length along the product widthwise direction W of the leg hole stretch units 100 when a product (disposable diaper 10) provided with the leg hole stretch units 100 for measurement is expanded to the maximum extent so that the product is not destructed. Furthermore, the length in the natural state, that is a contracted state, is the length along the product widthwise direction W of the leg hole stretch units 100 when concavities and convexities by gathers are formed to a minimum by placing the product on a flat surface and adding little load that stretches the product in the widthwise direction. Additionally, it is preferable to measure the length in the each of the above-described states along the lines at the end inside in the product widthwise direction W of the stretch sheet 200 when the leg hole stretch units 100 are curved as in the present embodiment.

It is preferable that the meandering portion formed at the leg hole stretch units 100 have an amplitude A between 2.5 mm and 20 mm in the product widthwise direction W. When a predetermined inflection point (for example, inflection point P4) is used as a basis, the amplitude A is a distance between the inflection point P4 and an intersection between a straight line through two inflection points (such as inflection points P3, P5) which are adjacent to the inflection point P4, and a line that is orthogonal to the straight line and passes through the inflection point (P4). Additionally, the starting point of an amplitude of a convex unit 110 is at an intersection (E1 shown in FIGS. 1 and 2) of a center in the product lengthwise direction L of the target tape 65 and the end edge of the side flaps 70, and the starting point of an amplitude of a convex unit 120 is at a base end of the fastening tape 90 on the side of the crotch unit 25 (E2 shown in FIGS. 1 and 2).

Also, the amplitude A is a distance between the inflection point and the point noted above, which is measured when the disposable diaper 10 is in an open expanded condition. When the amplitude A is less than 2.5 mm, a concave and convex area cannot be well formed at the leg hole stretch units 100, and it will be harder to reduce the pressure on skin at the time of wearing the disposable diaper 10. Moreover, when the amplitude A exceeds 20 mm, the leg hole stretch units 100 are likely to be tucked in between the body of a wearer and the disposable diaper 10 by the movement of the wearer, thus it is not possible to exhibit the functions of each concave and convex area. Furthermore, concavities and convexities will be more visible, so that leg holes will have a poor visual appearance while the disposable diaper 10 is being worn.

The open expanded condition is the state when the whole disposable diaper 10 is opened as shown in FIG. 1. Specifically, this state is provided by extending, through visual confirmation, the gather regions that have an elastic element for expansion and contraction, enough to show few gathers when holding the diaper on a flat stand.

The amplitude A can also be checked by removing only a non-elastic member which forms the leg holes (nonwoven fabric forming a sidetop or a backsheet in the present embodiment), from the main body of the disposable diaper 10.

At the front end and rear end of the leg hole concave units 35, the convex units 110, 120 are formed and protrude more toward outside in the product widthwise direction W than the other sections of the leg hole concave units 35. At the crotch unit 25, a crotch convex unit 130 is formed. One of the front and rear convex units 110 and 120 has a width in the product widthwise direction W and a length in the product lengthwise direction L respectively larger than a width in the product widthwise direction and a length in the product lengthwise direction of the crotch convex unit 130.

Figure 4:
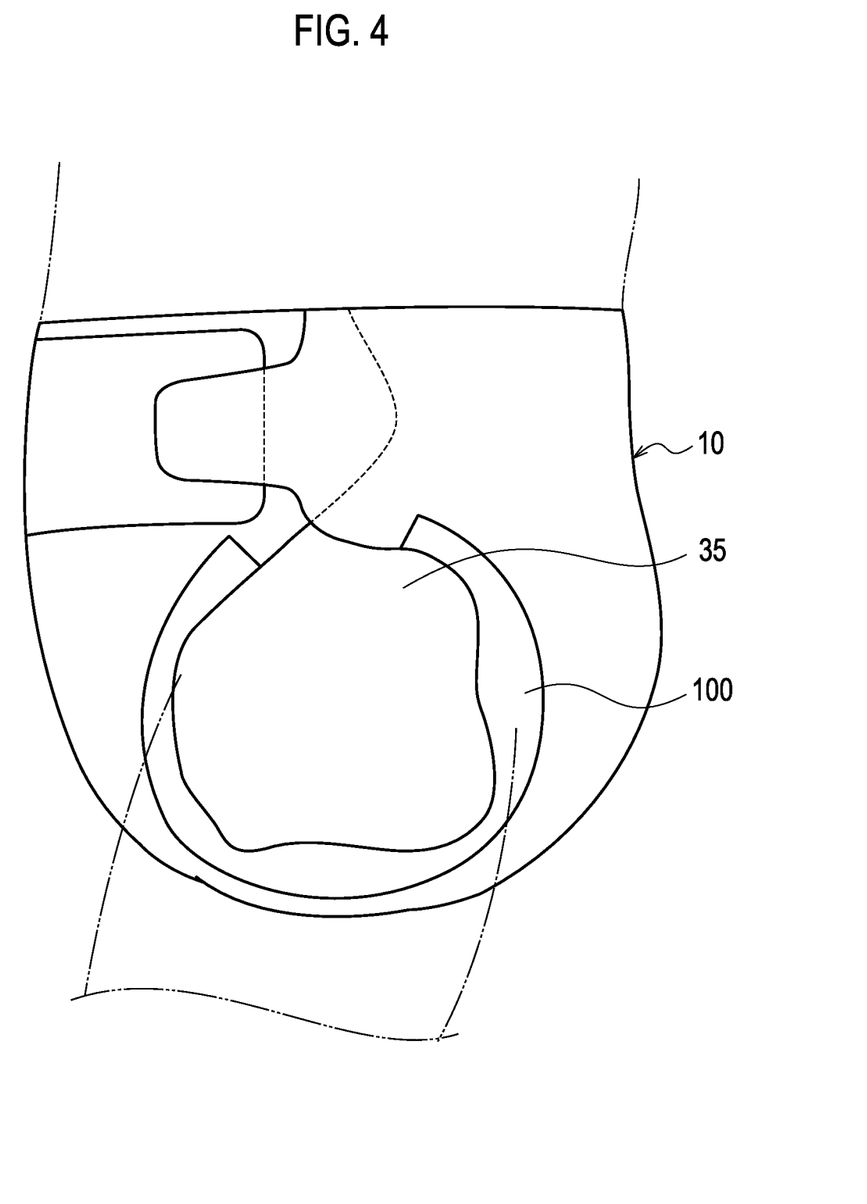
FIG. 4 is a diagram schematically illustrating the state when the disposable diaper 10 according to the embodiment of the present invention is worn by a wearer.

FIG. 4 is a diagram schematically illustrating the state when the disposable diaper 10 is worn by a wearer. Since stress can easily concentrate on the front end and rear end of the leg hole concave units 35, it is preferable that the pressure on skin be dispersed further by forming the convex units 110, 120. More specifically, stress is likely to concentrate on those ends since they are near the base ends of the fastening tapes 90 and also the target tape 65 arranged at the front waistline unit 20 and are the front and rear ends of the leg hole concave units 35. Also, those ends may lie on top of each other in front and back of the disposable diaper 10 when the diaper is being worn. Consequently, it is preferable that a convex shape be created to disperse the pressure on skin.

It is required that a convex unit 130 and a concave unit 140 formed at the crotch unit 25 not only reduce the pressure on skin but also fit to the body of a wearer. It is also required that the pressure on skin be reduced further at the location near the front and rear ends of the leg hole concave units 35. With the shape as described in the present embodiment, the load itself that is added on the leg hole stretch units 100 by the movement of a wearer is reduced, and at the same time, the pressure on skin is prevented from concentrating locally.

A concave unit 125 is recessed toward the center side in the product widthwise direction W so as to run along a curve S1 along the legs of a wearer, so that the unit is likely to fit along the groin of a wearer. Consequently, the stretch sheet 200 better fits to a wearer, and a section from the front waistline unit 20 to the crotch unit 25 of the disposable diaper 10 lies stably along the body, regardless of the movements of a wearer. For instance, even when a wearer makes a leg movement that may narrow the width of the absorber 40, the concave unit 125 continues to stay fit in the groin and the absorber 40 stays wide without narrowing. Thus, it is preferable that there are concave units, like the concave unit 125, at a location closer to the front waistline portion 20 than the center in the product lengthwise direction L of the disposable diaper 10.

The convex unit 130 is formed at a location that corresponds to the crotch unit 25 of a wearer. The crotch unit 25 is sandwiched between two leg holes of a wearer and is an area where a distance between the right and left leg holes is short, so that the leg hole stretch units 100 are likely to be sandwiched between the absorbent body 15 and a wearer's body and be easily tucked in toward inside the disposable diaper 10. Therefore, it is preferable that the leg hole stretch units 100 cover the body more widely, so the convex unit 130 can prevent bodily waste from leaking from the absorbent body 15 more completely. Additionally, as described above, as the concave unit 125 fits the groin, the convex unit 130 is further prohibited from getting inside the diaper.

The concave unit 140 and a concave unit 160 are formed closer to the rear waistline unit 30 than the center in the product lengthwise direction L of the disposable diaper 10. A convex unit 150 is formed between the concave unit 140 and the concave unit 160. In other words, the concave unit 140 and the concave unit 160 are formed with a predetermined distance therebetween in the product lengthwise direction L. Such a shape can prevent, when the disposable diaper 10 is worn on the body of the wearer with the fastening tapes 90, the leg hole stretch unit 100 (or the leg side gathers 80) from being caught with a wearer's body while failing to keep the crotch unit close to the wearer's crotch and to cover the front waistline (ventral).

The concave unit 140 is formed to prevent the leg hole concave units 35 from being caught at the narrow crotch unit while being passed through a wearer's buttocks throughout the crotch unit up until it abuts the ventral. Moreover, the concave unit 160 is formed to prevent the leg hole stretch units 100 on the side of the rear waistline unit 30 from being caught with a wearer's body and thus from improperly fixing the fastening tapes 90 while the tapes 90 existing at the sides of the rear waistline unit 30 being fixed to the target tape 65, and also to prevent the leg hole stretch unit 100 ranging from the fastening tapes 90 toward the side of the rear waistline unit 30, from being worn in a stretched manner. If a diaper is worn while the leg hole stretch units 100 are caught with a wearer's body and in a stretched manner, force is added by the movements of wearer's legs in a downward direction, letting the disposable diaper 10 slide downward. Thus, even if the disposable diaper 10 is held around a waistline with the fastening tapes 90, the diaper is likely to slide down, which is not preferable.

The convex unit 150 is formed, along with the adjacent concave unit 140 and concave unit 160, so as to alleviate the pressure on skin mainly from a location corresponding to a wearer's buttocks to a location corresponding to his dorsal. Furthermore, as the convex unit 150 widely covers a wearer's buttocks, the diaper has a better appearance and can also provide a good sense of security in that both leakage of bodily waste and position gap of the disposable diaper 10 are unlikely to occur, by providing more coverage.

As explained above, four convex units and three concave units are formed at the leg hole stretch unit 100. Out of four convex units, two convex units (the convex unit 110, 120) are formed at the front end and rear end of the leg hole concave units 35 in the product lengthwise direction L. Out of three concave units, two concave units (the concave units 140, 160) are formed closer to the rear waistline unit 30 than a center CT (see FIG. 1) in the product lengthwise direction L.

Additionally, out of four convex units, one convex unit (convex unit 130) is formed closer to the front waistline unit 20 than the center CT. Out of three concave units, one concave unit (the concave unit 125) is formed between the convex unit 110 formed at the front end of the leg hole concave unit and the convex unit 130 that is formed closer to the front waistline unit 20 than the center CT. Furthermore, out of four convex units, one convex unit (the convex unit 150) is formed between the two concave units 140, 160 that are formed closer to the rear waistline unit 30 than the center CT.

Also, it is preferable in the present embodiment that a thickness outside in the product widthwise direction W of the leg hole stretch unit 100 be thinner than a thickness inside in the product widthwise direction W of the leg hole stretch unit 100 at a location that corresponds to at least one of the front waistline unit 20 and the crotch portion 25 as shown in FIG. 3. Specifically, in order to provide the thickness of the end edges of the leg hole stretch units 100 that are thinner in the product widthwise direction W than inside in the product widthwise direction W, there are fewer laminated sheets near the end edges. In the present embodiment, as shown in FIG. 3, provided are three sheets (the leg side gathers 80, the stretch sheet 200 and the back sheet 60) at the side edge portion (T1 in the figure) in the product widthwise direction W of the leg hole stretch unit 100. On the other hand, four sheets (the leakage-preventing film 55 are added) are provided in the inner portion (T2 in the figure) in the product widthwise direction W of the leg hole stretch unit 100.

Here, the thickness is measured as follows.

First, as a sample, the leg hole stretch unit 100 is cut out of the disposable diaper 10.

Second, the sample is extended enough to show few folds on the surface of the sample when holding the sample in a flat state.

Third, in the state, the thickness of the measurement-target region is measured by a thickness gauge (for example, OZAKI MFG. CO., Dial Thickness Gauge) with load of 2.5 gf/cm$^2$. A sequence of the measurement is performed under the condition of 20° C. and 60% RH.

Alternatively, the thickness can be calculated based on the number of sheets disposed in the measurement-target region.

At a section of the disposable diaper 10 corresponding to the wearer's groin, the disposable diaper 10 is most likely to dig in skin by the movement of legs. Thus, by making the end edge portions thinner in the product widthwise direction W of the leg stretch units 100 than inside in the product widthwise direction W, the leg hole stretch units 100 are likely to fit better from inside toward outside in the product widthwise direction W at the time of wearing the disposable diaper 10. As the side edges in the product widthwise direction W of the leg hole stretch units 100 are made thinner, the leg hole stretch units 100 are more likely to fit better on the skin. Particularly, by providing in a location that corresponds to the concavity of a wearer's body, such as the groin, the leg hole stretch units 100 can fit better and have more stability in the groin. At the same time, the pressure on the skin from the leg hole stretch units 100 can be dispersed effectively and stably. Consequently, the leg hole stretch units 100 will be more fitting and stable around the groin area, and the pressure on the skin from the leg hole stretch units 100 can be dispersed effectively and stably.

Additionally, stretch sheets and non-stretch sheets configuring the leg hole stretch units 100 are bonded by pattern coating an adhesive line so as to exist adhesive sections and non-adhesive sections by spiral coating or Ω coating. Furthermore, the stretch sheet is a nonwoven cloth sheet including elastic fiber with elastomer properties, and the non-stretch sheet is also a nonwoven cloth sheet. Specifically, there is no film sheet at the ends of the leg hole concave units 35. In the configuration mentioned above, since the fibers of the nonwoven cloth sheets mesh with each other, the ends of the leg hole concave units 35 do not open when the disposable diaper 10 is being worn. Also, there is no adhesive at the ends of the leg hole concave units 35 as a whole, allowing for more flexible leg hole stretch units 100.

Additionally, as a result of the coating mentioned above, it is possible to prevent the stretch properties of the stretch sheet from being impaired by the non-stretch sheet, and it is also possible to improve the fitness to the body of the wearer around the leg hole concave units 35.

(3) Operation and Effect

As described above, the leg hole stretch units 100 extend in the product lengthwise direction L at an area where the leg hole concave units 35 are formed. The end edges in the product widthwise direction W of the leg hole stretch units 100 are meandering in the product lengthwise direction L, and the distance between the end edge in the product widthwise direction W of the leg hole stretch units 100 and the center line CL changes from the front waistline unit 20 toward the rear waistline unit 30. Provided are a plurality of inflection points P where an amount of change in distances starts decreasing instead of increasing and inflection points P where an amount of change in distances starts increasing instead of decreasing.

Such a meandering leg hole stretch unit 100 can effectively prohibit the unit 100 from digging into the skin of a wearer, thereby reducing skin irritation of a wearer. Also, as described above, such a meandering leg hole stretch unit 100 can completely prevent the leakage of bodily waste. In other words, according to the disposable diaper 10, the leakage of bodily waste is prevented completely, and at the same time, irritation to the skin around the leg holes of a wearer can be reduced further.

Additionally, when the disposable diaper 10 was tested in comparison with a conventional disposable diaper having no meandering leg hole stretch units 100, it was confirmed that there were hardly any marks (slight redness of the skin) around the groin of a wearer while the fitting around the legs were increased.

(4) Other Embodiments

So far, the present invention is disclosed through the above embodiment of the present invention. However, it should not be interpreted that the statements and drawings constituting a part of the present disclosure limit the present invention. From this disclosure, a variety of alternate embodiments, examples, and applicable techniques will become apparent to one skilled in the art.

Figure 5:
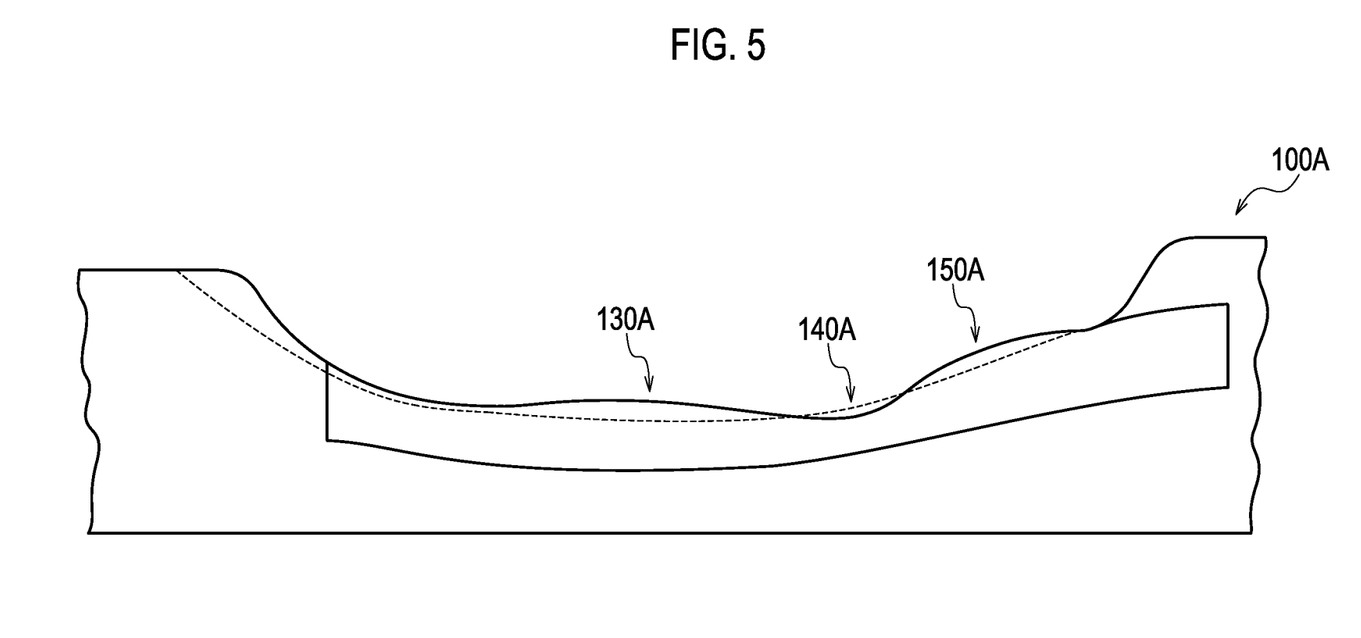
FIG. 5 is an enlarged plan view of a leg hole stretch unit 100A according to a modification of the present invention.

For example, the shape of the leg hole stretch units 100 mentioned above may be modified as below. FIG. 5 is an enlarged plan view of a leg hole stretch unit 100A according to a modification of the present invention. As shown in FIG. 5, convex units 130A and 150A and a concave unit 140A may be formed smaller than the convex units 130 and 150 and the concave unit 140 of the leg hole stretch units 100 described above. In other words, the amplitude A of the leg hole stretch units 100A may be smaller than that of the leg hole stretch units 100.

In the above-described embodiment, the stretch sheet 200 configuring the leg hole stretch units 100 extends to the ends outside in the product widthwise direction W as shown in FIG. 3. However, in consideration of the ease of production, it is unnecessary to extend the stretch sheet 200 to the ends outside in the product widthwise direction W. Specifically, the ends of the stretch sheet 200 outside in the product widthwise direction W may be located further inside in the product widthwise direction W than the ends of the backsheet 60 and the leg side gathers 80, etc. outside in the product widthwise direction W. Moreover, in this case, it is preferable that a distance between the ends of the stretch sheet 200 outside in the product widthwise direction W and the ends of the backsheet 60 and the leg side gathers 80, etc., outside the product widthwise direction W be 7 mm or less.

Furthermore, although an open-type disposable diaper with the fastening tapes 90 is explained as an example in the embodiment described above, the present invention may be applied to a pant-type disposable diaper.

As described above, it is of course that the present invention includes various embodiments and the like not described here. Therefore, the technical range of the present invention is to be defined only by the inventive specific matter according to the adequate claims from the above description.

REFERENCE SIGNS LIST

10 . . . disposable diaper
15 . . . absorbent body
20 . . . front waistline unit
25 . . . crotch unit
30 . . . rear waistline unit
35 . . . leg hole concave unit
40 . . . absorber
40a . . . absorbent core
40b . . . core wrap
50 . . . topsheet
55 . . . leakage-preventing film
60 . . . backsheet
65 . . . target tape
70 . . . side flaps
80 . . . leg side gathers
90 . . . fastening tape
100, 100A . . . leg hole stretch unit
110, 120, 130, 130A, 150, 150A . . . convex unit
125, 140, 140A, 160 . . . concave unit
200 . . . stretch sheet

The invention claimed is:

1. A disposable diaper, comprising:
a front waistline unit;
a rear waistline unit;
a crotch unit;
an absorbent body elongated in a product lengthwise direction and including
  a liquid retaining absorber, and
  end sides opposing each other in a product widthwise direction of the absorbent body, the product widthwise direction crossing the product lengthwise direction;
side flaps arranged at the end sides of the absorbent body; and
sheet-shaped leg hole stretch units arranged at side edges of the side flaps in the product widthwise direction,
wherein
  the side flaps include leg hole concave units that are recessed toward a center of the absorbent body in the product widthwise direction,
  the leg hole concave units have end edges opposing each other in the product widthwise direction,
  the sheet-shaped leg hole stretch units extend in the product lengthwise direction in an area where the leg hole concave units are formed and are partially stretchable at least along the product lengthwise direction,
  the leg hole stretch units have end edges opposing each other in the product widthwise direction and meandering in the product lengthwise direction,
  a distance between (i) each of the end edges of the leg hole stretch units in the product widthwise direction and (ii) a straight line that passes through the center of the absorbent body in the product widthwise direction and is parallel to the product lengthwise direction changes from the front waistline unit toward the rear waistline unit,
  each of the leg hole stretch units includes a plurality of first turning points where an amount of change in the distance starts decreasing, instead of increasing, from the front waistline unit toward the rear waistline unit, and a plurality of second turning points where an amount of change in the distance starts increasing, instead of decreasing, from the front waistline unit toward the rear waistline unit, said first and second turning points being configured to cause at least a part of the end edge of each of the leg hole stretch units to meander in the product lengthwise direction, the leg hole stretch units are arranged along the end edges of the leg hole concave units, at least a part of the end edge of each of the leg hole concave units meanders in the product lengthwise direction, at least one of the leg hole concave units includes
a front convex unit at a front end of the at least one leg hole concave unit;
a rear convex unit at a rear end of the at least one leg hole concave unit; and
a crotch convex unit at the crotch unit, and one of the front and rear convex units has a width in the product widthwise direction and a length in the product lengthwise direction respectively larger than a width in the product widthwise direction and a length in the product lengthwise direction of the crotch convex unit.

2. The disposable diaper according to claim 1, wherein each of the leg hole stretch units has a width in the product widthwise direction between 5 mm and 45 mm when in a natural state.

3. The disposable diaper according to claim 1, wherein
each of the leg hole stretch units has a meandering section, and
an amplitude of the meandering section in the product widthwise direction is between 2.5 mm and 20 mm.

4. The disposable diaper according to claim 1, wherein
said front and rear convex units are positioned further toward outside in the product widthwise direction than any other sections of the at least one leg hole concave unit.

5. The disposable diaper according to claim 1, wherein
the leg hole stretch units include inner edges opposite to the end edges of the leg hole stretch units in the product widthwise direction, and
a thickness of the end edges of the leg hole stretch units is smaller than a thickness of the inner edges of the leg hole stretch units at a location that corresponds to at least one of the front waistline unit and the crotch unit.

6. The disposable diaper according to claim 1, wherein
the leg hole stretch units have the degree of stretch between 1.5 times and 2.4 times.

7. The disposable diaper according to claim 1, wherein the at least one of the leg hole concave units includes four convex units and three concave units,
the four convex units include:
the front convex unit;
the crotch convex unit;
the rear convex unit; and
another rear convex unit positioned between said rear convex unit and the crotch convex unit in the product lengthwise direction; and
the three concave units include:
a front concave unit between the front convex unit and the crotch convex unit in the product lengthwise direction;
a rear concave unit between the another rear convex unit and the rear convex unit in the product lengthwise direction; and
a crotch concave unit between the another rear convex unit and the crotch convex unit in the product lengthwise direction.

8. The disposable diaper according to claim 1, wherein at least the part of the end edge of each of the leg hole stretch units coincides, in the product lengthwise direction, with the part of the end edge of the corresponding leg hole concave unit.

9. The disposable diaper according to claim 8, wherein each of the leg hole stretch units includes an elastic nonwoven sheet.

10. The disposable diaper according to claim 9, wherein said elastic nonwoven sheet of each of the leg hole stretch units has opposite ends in the product lengthwise direction, and
the end edges of the leg hole concave units extend beyond the opposite ends of the elastic nonwoven sheets in the product lengthwise direction.

11. A disposable diaper comprising:
a front waistline unit;
a rear waistline unit;
a crotch unit;
an absorbent body elongated in a product lengthwise direction and including
a liquid retaining absorber, and
end sides opposing each other in a product widthwise direction of the absorbent body, the product widthwise direction crossing the product lengthwise direction;
side flaps arranged at the end sides of the absorbent body; and
sheet-shaped leg hole stretch units arranged at side edges of the side flaps in the product widthwise direction, wherein
the side flaps include leg hole concave units that are recessed toward a center of the absorbent body in the product widthwise direction,
the leg hole concave units have end edges opposing each other in the product widthwise direction,
the sheet-shaped leg hole stretch units extend in the product lengthwise direction in an area where the leg hole concave units are formed and are partially stretchable at least along the product lengthwise direction,
the leg hole stretch units have end edges opposing each other in the product widthwise direction and meandering in the product lengthwise direction,
a distance between (i) each of the end edges of the leg hole stretch units in the product widthwise direction and (ii) a straight line that passes through the center of the absorbent body in the product widthwise direction and is parallel to the product lengthwise direction changes from the front waistline unit toward the rear waistline unit,
each of the leg hole stretch units includes
a plurality of first turning points where an amount of change in the distance starts decreasing, instead of increasing, from the front waistline unit toward the rear waistline unit, and
a plurality of second turning points where an amount of change in the distance starts increasing, instead of decreasing, from the front waistline unit toward the rear waistline unit,
at least a part of the end edges of the leg hole concave units meanders in the product lengthwise direction, at least one of the leg hole concave units includes
a front convex unit at a front end of the at least one leg hole concave unit;
a rear convex unit at a rear end of the at least one leg hole concave unit; and
a crotch convex unit at the crotch unit, and
one of the front and rear convex units has a width in the product widthwise direction and a length in the product lengthwise direction respectively larger than a width in the product widthwise direction and a length in the product lengthwise direction of the crotch convex unit.

12. The disposable diaper according to claim 11, wherein at least the part of the end edge of each of the leg hole stretch units coincides, in the product lengthwise direction, with the part of the end edge of the corresponding leg hole concave unit.

13. The disposable diaper according to claim 11, wherein each of the leg hole stretch units includes an elastic nonwoven sheet.

14. The disposable diaper according to claim 13, wherein
said elastic nonwoven sheet of each of the leg hole stretch units has opposite ends in the product lengthwise direction, and
the end edges of the leg hole concave units extend beyond the opposite ends of the elastic nonwoven sheets in the product lengthwise direction.

* * * * *